United States Patent [19]

Ratton

[11] Patent Number: 4,683,346

[45] Date of Patent: Jul. 28, 1987

[54] SELECTIVE PREPARATION OF MONOHALOHYDROQUINONES

[75] Inventor: Serge Ratton, Villefontaine, France

[73] Assignee: Rhone-Poulenc Specialites Chimiques, Courbevoie, France

[21] Appl. No.: 810,753

[22] Filed: Dec. 19, 1985

[30] Foreign Application Priority Data

Dec. 19, 1984 [FR] France ............................... 84 19748

[51] Int. Cl.$^4$ .............................................. C07C 39/10
[52] U.S. Cl. ...................................... 568/765; 568/779
[58] Field of Search ........................ 568/765, 779, 774

[56] References Cited

U.S. PATENT DOCUMENTS 1,912,744  6/1933  Bramer et al. ...................... 568/765

4,439,595  3/1984  Chiang ................................ 568/765
4,439,596  3/1984  Irwin ................................... 568/765

FOREIGN PATENT DOCUMENTS 2852645  6/1980  Fed. Rep. of Germany ...... 568/765
2274586  1/1976  France ................................ 568/765
0005132  1/1984  Japan ................................... 568/765
0563541  8/1944  United Kingdom ............... 568/765

*Primary Examiner*—Werren B. Lone
*Attorney, Agent, or Firm*—Burns, Doane, Swecker & Mathis

[57] ABSTRACT

Hydroquinone is selectively nascently chlorinated to monochlorohydroquinone, by reacting same with an aqueous solution of hydrochloric acid and hydrogen peroxide, in the presence of an organic solvent for, and inert to, said hydroquinone.

11 Claims, No Drawings

SELECTIVE PREPARATION OF MONOHALOHYDROQUINONES

BACKGROUND OF THE INVENTION

1. Field of the Invention

The present invention relates to the preparation of monohalohydroquinones, and especially to the preparation of monochlorohydroquinone by halogenation of hydroquinone.

2. Description of the Prior Art

Monohalohydroquinones, and in particular monochloro and monobromohydroquinones, are important industrial compounds useful as intermediates in organic synthesis, in the photographic industry (see U.S. Pat. Nos. 2,748,173 and 1,912,744) or as dihydroxylated compounds for the preparation of anisotropic polyesters (see U.S. Pat. No. 4,118,372 and French patent application No. 79/24,135, published under No. 2,465,758). Monochlorohydroquinone, in particular, is in marked demand for these uses.

Although various syntheses for the preparation of the monohalohydroquinones, and in particular of monochlorohydroquinone, have been proposed to this art, starting with compounds such as p-benzoquinone and ortho-chlorophenol, the most advantageous method from an industrial standpoint consists in the halogenation of hydroquinone, a common and inexpensive material. To this end, several processes have been described. Thus, in U.S. Pat. No. 1,912,744 it was recommended to prepare monochloro- and monobromohydroquinones by passing chlorine or bromine into a suspension of hydroquinone in carbon tetrachloride. According to U.S. Pat. No. 2,748,173, monochlorohydroquinone is prepared by passing chlorine gas into a concentrated solution of hydroquinone in aqueous acetic acid. These two processes have the major disadvantage of leading, whatever precautions are taken, to the concomitant formation of 2,3- and/or 2,5-dichlorohydroquinones in amounts which become greater as the degree of conversion of the hydroquinone increases.

To remedy this disadvantage, it was proposed, in published Japanese Application No. 56/45,433, to carry out the chlorination of hydroquinone using dilute hydrochloric acid in the presence of copper salts or iron salts as catalysts, and working under an oxygen pressure. Although this process appears to be conducive to more selective production of monochlorohydroquinone, its value is reduced by the need to resort to pressure-resistant equipment and to the use of metal salts. In U.S. Pat. Nos. 4,439,595 and 4,439,596 it was proposed to replace chlorine by sulfuryl chloride and to perform the chlorination in alkyl esters or in glacial acetic acid in order to obtain mixtures having a high monochlorohydroquinone content, the mixtures being directly usable for the preparation of the corresponding diacetate intended for the production of anisotropic polyesters. In this case, the presence of significant amounts of dichlorohydroquinones and of unconverted hydroquinone is not prejudicial to the desired object; the yields of dichlorohydroquinone relative to the hydroquinone converted remain greater than 10% and the degree of conversion of hydroquinone less than 90%.

It has also been proposed to conduct the halogenation of hydroquinone using halogens in the nascent state, formed "in situ" by oxidation of a hydracid with an oxidizing agent. Thus, in British Pat. No. 563,541, a process has been described for preparing mono- or polychlorohydroquinones via the nascent chlorine formed by adding manganese dioxide to a suspension of hydroquinone in concentrated hydrochloric acid. The use of the manganese oxide limits the industrial value of this process because it involves the handling and addition of a solid material to the suspension of hydroquinone in hydrochloric acid, and requires a laborious regeneration of the manganese oxide from the manganese chloride by-product. In French patent application No. 73/20,507, published under No. 2,187,735, it has been proposed to conduct the halogenation of various aromatic compounds, including hydroquinone, using a halogen (chlorine, bromine, iodine)/hydrogen peroxide system in order to recover, in the form of halogen, the hydracid released by the direct halogenation of the aromatic compound. This process hence employs a first ordinary stage of halogenation of the substrate with a deficit of halogen relative to stoichiometry, and a second stage of halogenation of the unconverted substrate using the halogen formed "in situ" by oxidation of the hydracid, which is a by-product, with hydrogen peroxide. This process is advantageously carried out in a two-phase system containing an aqueous phase and an organic phase. It has been found that, in the case of the chlorination of hydroquinone, this process does not remedy the disadvantages of the earlier processes, particularly as regards the formation of polychlorohydroquinones; furthermore, a large amount of hydroquinone undergoes, under these conditions, oxygenation by the hydrogen peroxide and/or the nascent chlorine, especially when the medium is heterogeneous.

Thus, despite the extensive research heretofore conducted in this art, serious need continues to exist for a process by which hydroquinone can be halogenated simply, more selectively and more completely. Cf. *Chemical Abstracts*, 95, No. 9, p. 738, No. 80474 g (1981); U.S. Pat. No. 3,929,907; French Pat. No. 950,265.

SUMMARY OF THE INVENTION

Accordingly, a major object of the present invention is the provision of an improved process for the halogenation of hydroquinone to monohalohydroquinone, and which enables the concurrent formation of dihalohydroquinones to be significantly reduced.

A second object of the present invention is the provision of an improved process for the halogenation of hydroquinone to monohalohydroquinone wherein the degree of conversion of hydroquinone, and consequently the productivity of the process, is increased.

A third object of the present invention is the provision of an improved process for the halogenation of hydroquinone to monohalohydroquinone which can more easily be carried out industrially by virtue of the nature of the reagents and the reaction conditions.

A fourth object of the invention is the provision of an improved process for the chlorination of hydroquinone to monochlorohydroquinone using chlorine in the nascent state, thus avoiding or limiting the inopportune oxidation of hydroquinone.

Briefly, the present invention features a process for the chlorination of hydroquinone principally to monochlorohydroquinone, using chlorine in the nascent state, and wherein the hydroquinone is reacted with an aqueous solution of hydrochloric acid and hydrogen peroxide in the presence of an organic solvent for hydroquinone which is inert under the conditions of the reaction.

DETAILED DESCRIPTION OF THE INVENTION

More particularly according to the present invention, those solvents for hydroquinone which are suitable are those which are inert under the conditions of the reaction, that is to say, compounds which do not give rise to chlorination reactions with nascent chlorine and/or hydrochloric acid, and/or which are not capable of being oxidized by hydrogen peroxide. Among these "inert" compounds, those which have little or no nucleophilic character are preferably employed.

In this respect, alkanoic acids and aliphatic or heterocyclic ethers are most especially suitable. As examples of alkanoic acids, acetic acid, propionic acid, n-pentanoic acid and n-hexanoic acid are representative; lower alkanoic acids, and especially acetic acid, are preferably used. Ethers constitute a preferred class of solvents for hydroquinone; ethyl ether, n-propyl ether, isopropyl ether, n-butyl ether, dioxane and diglyme (diethylene glycol dimethyl ether) are representative. Among solvents for hydroquinone which are inert under the conditions of the reaction, there are preferably employed those which are miscible with aqueous hydrochloric acid solutions at the selected concentration, under the temperature conditions adopted, and which are, in this respect, capable of providing for at least partial miscibility of the aqueous hydrochloric acid solution and the organic solution of hydroquinone during the reaction, and consequently of providing for the best possible contact between the nascent chlorine and the hydroquinone. From this standpoint, ethyl ether, isopropyl ether, dioxane and diglyme are preferred. Isopropyl ether is most especially suitable. The miscibility of the organic solution of hydroquinone with the aqueous hydrochloric acid solution does not depend only upon the nature of the solvent, but also upon the concentration of the aqueous hydrochloric acid solution and the temperature. The choice of a solvent for hydroquinone which is miscible, under the conditions of the reaction, with the aqueous hydrochloric acid solution enables the chlorination to be preferentially carried out in a homogeneous phase.

It has now been found, quite unexpectedly in light of the heretofore state of the art, that the best results are obtained when the hydroquinone/hydrochloric acid/water/solvent reaction mixture is homogeneous, that is to say, forms only a single liquid phase. Under these conditions, it is possible to obtain excellent yields of monochlorohydroquinone, by limiting the formation of dichlorohydroquinones and the possible oxidation of hydroquinone by the nascent chlorine and/or by the hydrogen peroxide observed under the conditions recommended by the above-mentioned British Pat. No. 563,541 and published French patent application No. 2,187,735.

Thus, the present invention more specifically features a process for the chlorination of hydroquinone, principally to monochlorohydroquinone, with chlorine in the nascent state, and wherein the hydroquinone is reacted with an aqueous solution of hydrochloric acid and hydrogen peroxide, in the presence of an organic solvent for hydroquinone which is inert and miscible, under the conditions of the reaction, with the aqueous hydrochloric acid solution of selected concentration.

Still more preferably, the present invention features an improved process for the chlorination of hydroquinone, principally to monochlorohydroquinone, using chlorine in the nascent state, according to which hydroquinone is reacted with an aqueous solution of hydrochloric acid and hydrogen peroxide in the presence of an inert solvent for hydroquinone which is miscible with the aqueous hydrochloric acid solution while maintaining the reaction medium homogeneous throughout the duration of the reaction.

Although the concentration of the aqueous hydrochloric acid solution may vary over wide limits, it is advantageously selected, for a given solvent, such as to provide preferably for the greatest possible miscibility of the solvent with the aqueous hydrochloric acid solution under the temperature conditions adopted; in the final analysis, this concentration, expressed in moles of hydrochloric acid per liter of aqueous solution, depends, for a given temperature, to some extent on the nature of the solvent selected. Aqueous hydrochloric acid solutions of a concentration equal to at least 7 moles per liter, and preferably to at least 8 moles per liter, are preferably employed. There is no critical upper limit to the concentration of the hydrochloric acid solution. In practice, however, there is no purpose in exceeding a concentration of 12 moles per liter; a concentration of 9 to 11 moles of HCl per liter of solution is very suitable.

The amount of hydrochloric acid, expressed as moles of HCl per mole of hydroquinone, is not critical, provided it is at least in the region of the stoichiometric amount required for the reaction to proceed, that is to say, in the region of 1 mole per mole of hydroquinone. The use of an amount of hydrochloric acid less than 1 mole per mole of hydroquinone results in incomplete conversion of the hydroquinone and offers no particular advantage. The amount of hydrochloric acid is preferably at least 0.9 mole per mole of hydroquinone; although there is no critical upper value, it is of no advantage to use more than 50 moles of HCl per mole of hydroquinone.

The relative amounts of solvent and aqueous hydrochloric acid solution are not critical. When, according to a preferred embodiment of the invention, the process is carried out in a homogeneous phase, these amounts are selected such as to provide for good miscibility of the organic solution of hydroquinone and the aqueous hydrochloric acid solution; the amounts which are appropriate for attaining this objective depend upon the nature of the solvent, the concentration of the aqueous hydrochloric acid solution and the temperature, and hence must be determined in each particular case to provide for homogeneity of the reaction medium during most of the course of the reaction.

The amount of hydrogen peroxide, expressed as moles of $H_2O_2$ per mole of hydroquinone, is preferably in the region of the stoichiometric amount, that is to say, in the region of 1 mole per mole. In practice, the amount of hydrogen peroxide ranges from 0.9 to 1.2 mole of $H_2O_2$ per mole of hydroquinone, and preferably from 1 to 1.1 mole per mole of hydroquinone.

Although the concentration of the aqueous hydrogen peroxide solution, expressed as weight of $H_2O_2$ per 100 g of solution, is in no way critical, it is preferable to employ solutions of sufficient concentration such that the volume of the reacting mass is not unduly increased. Moreover, the use of dilute solutions of hydrogen peroxide plays a part in lowering the concentration of the aqueous hydrochloric acid solution as the reaction proceeds, as a result of the water introduced which is added to the water formed as the hydracid oxidizes. When it is desired to maintain the homogeneity of the medium for as long as possible, it is preferable to employ aqueous hydrogen peroxide solutions having a concentration in the range of from 20 to 90% by weight.

The temperature at which the chlorination according to the present invention is carried out can also vary over wide limits. In practice, a temperature of from 0° to 150° C., and preferably from 10° to 100° C., is very suitable. The reaction can be carried out at atmospheric pressure or at a higher pressure if that proves necessary, for example, at the pressure intrinsically generated by the reaction medium.

The process according to the invention is especially simple to carry out; in effect, it is only necessary to gradually add, under stirring, the hydrogen peroxide solution into a reaction vessel containing the aqueous hydrochloric acid solution and the organic solution of hydroquinone. When, according to a preferred embodiment of the invention, it is desired to conduct the reaction in a homogeneous phase, the reaction conditions are selected such that the reaction medium remains homogeneous, preferably until the addition of hydrogen peroxide is substantially completed. When this addition is completed, it is possible, depending upon the particular case, to maintain the reaction medium stirred and at the temperature selected for a period of time to be determined in each case.

When the reaction is completed, the reaction mixture is treated to recover the monochlorohydroquinone. When the procedure has been carried out in a homogeneous phase, it is appropriate to add to the reaction mixture an amount of water intended to cause segregation of an acidic aqueous phase and an organic phase containing the monochlorohydroquinone, dichlorohydroquinones and, where relevant, unconverted hydroquinone, and the aqueous and organic phases are then separated by decantation. The aqueous phase is washed with a solvent to extract the chlorohydroquinones and hydroquinone therefrom. The solvent used during the reaction is generally selected therefor. The extract and the organic phase are combined, and the solvent is driven off; the chlorohydroquinones and hydroquinone are separated and recovered by the customary means. When the reaction has proceeded in a heterogeneous phase, the aqueous and organic phases are separated by decantation and the aqueous phase is then treated as above.

The process according to the invention is especially well suited for being carried out as a continuous process.

In order to further illustrate the present invention and the advantages thereof, the following specific examples are given, it being understood that same are intended only as illustrative and in nowise limitative.

EXAMPLE 1

Into a 250 ml three-necked flask equipped with a dropping funnel, a condenser and a stirrer, the following materials were introduced:
(i) Hydroquinone: 11 g—0.1 mole—photographic grade;
(ii) 10N Hydrochloric acid: 80 ml—0.8 mole.

40 ml of pure diisopropyl ether were then added slowly, under stirring. The hydroquinone dissolved and a homogeneous solution formed at room temperature. With the temperature maintained at 20°–23° C., 11.42 g of 29.8% hydrogen peroxide, equivalent to 0.1 mole, were slowly run into the mixture. The time necessary for this was 1 hr, 20 min, and the reaction medium became heterogeneous when this addition was completed. The mixture was maintained stirred at room temperature for 30 minutes, and the entire mixture was then transferred to a separating funnel. The two phases were separated, the organic phase was recovered and the aqueous phase was extracted four times with 50 m of diisopropyl ether. The organic phases were combined and the diisopropyl ether was then evaporated using a rotary evaporator. A powdery white solid product weighing 14.82 g was obtained. The precipitate, analyzed by high pressure liquid chromatography, contained the following products:
(1) Hydroquinone: 0.097 g–0.00825 mole;
(2) Monochlorohydroquinone: 12.11 g–0.08382 mole;
(3) 2,5-Dichlorohydroquinone: 0.847 g–0.00473 mole;
(4) 2,3-Dichlorohydroquinone: 0.3 g–0.00168 mole;
which corresponded to the following results:
(a) Conversion rate of hydroquinone: 91.75%
(b) Monochlorohydroquinone yield with respect to the hydroquinone converted: 91.35%
(c) 2,5-Dichlorohydroquinone yield with respect to the hydroquinone converted: 5.15%
(d) 2,3-Dichlorohydroquinone yield with to the hydroquinone converted: 1.85%. The above solid product (14.82 g) was placed in 75 ml of pure acetic anhydride. 30 mg of para-toluene-sulfonic acid were added.

The mixture was brought to a temperature of 100° C. for 3 hours, after which time compounds bearing a free phenol group were no longer detected (analysis by thin layer chromatography).

The solution was assayed by high pressure liquid chromatography. The following composition was determined:
(1) Hydroquinone diacetate: 1.615 g–0.00835 mole;
(2) Monochlorohydroquinone diacetate: 19.10 g–0.08364 mole;
(3) 2,5-Dichlorohydroquinone diacetate: 1.141 g–0.00433 mole;
(4) 2,3-Dichlorohydroquinone diacetate: 0.400 g–0.00152 mole.

This corresponded to the following results, expressed with respect to the hydroquinone initially subjected to the chlorination:
(a) Conversion rate of hydroquinone: 91.67%
(b) Monochlorohydroquinone diacetate yield with respect to the hydroquinone converted: 91.24%
(c) 2,5-Dichlorohydroquinone diacetate yield with respect to the hydroquinone converted: 74.7%
(d) 2,3-Dichlorohydroquinone diacetate yield with respect to the hydroquinone converted: 1.7%.

EXAMPLE 2

Into a 250 ml three-necked flask equipped with a dropping funnel, a condenser and a stirrer, the following materials were introduced:
(i) Hydroquinone: 11 g (0.1 mole) technical grade;
(ii) 10 N Hydrochloric acid: 120 ml (1.2 mole);
(iii) Pure diisopropyl ether: 40 ml.

The mixture was homogeneous at room temperature. With the solution maintained at between 22° and 25° C., 12.1 g of 29.5% hydrogen peroxide, equivalent to 0.105 mole, were then added. The time necessary for this was 1 hr, 05 min.

When the hydrogen peroxide had been completely introduced, the reaction mixture became heterogeneous. Stirring was maintained for approximately 1 hr. The reacting mass was then introduced into a separating funnel. The phases were separated, the organic phase was recovered, and the aqueous phase was washed four times with 50 ml of pure diisopropyl ether. The organic phases were combined and subjected to analysis by high pressure liquid chromatography. The following composition was determined:

(1) Hydroquinone: 0.465 g–0.00423 mole;
(2) Monochlorohydroquinone: 12.2 g–0.08445 mole;
(3) 2,5-Dichlorohydroquinone: 1.05 g–0.0059 mole;
(4) 2,3-Dichlorohydroquinone: 70.37 g–0.0021 mole;

which corresponded to the following results:
(a) Conversion rate of hydroquinone: 95.8%;
(b) Monochlorohydroquinone yield with respect to the hydroquinone converted: 88.2%;
(c) 2,5-Dichlorohydroquinone yield with respect to the hydroquinone converted: 6.15%;
(d) 2,3-Dichlorohydroquinone yield with respect to the hydroquinone converted: 2.2%

EXAMPLES 3 to 9

Using the procedure described above, the chlorination of the technical hydroquinone used in Example 2 was carried out, varying the conditions of the reaction. These conditions and the results obtained are reported in the Table below.

TABLE

| Examples | Hydrochloric acid Concentration | Volume | Solvent Nature | Volume | $H_2O_2$ in moles | T in °C. | DC HQ (1) % | YD CPHQ (2) % | YD DCPHQ (3) % |
|---|---|---|---|---|---|---|---|---|---|
| 3 | 10 N | 80 ml | IE (4) | 40 ml | 0.105 | 23 | 93.75 | 86.7 | 7.5 |
| 4 | 10 N | 160 ml | IE (4) | 80 ml | 0.105 | 23 | 94.6 | 85.6 | 9.5 |
| 5 | 10 N | 80 ml | BE (5) | 80 ml | 0.1 | 20 | 99.6 | 78.5 | 11.2 |
| 6 | 10 N | 80 ml | EE (6) | 40 ml | 0.105 | 20 | 84.5 | 86.38 | 10.05 |
| 7 | 10 N | 80 ml | dioxane | 60 ml | 0.105 | 28 | 91.75 | 86.7 | 10.92 |
| 8 | 10 N | 80 ml | diglyme | 40 ml | 0.105 | 23 | 90.25 | 84.9 | 9.87 |
| 9 | 10 N | 50 ml | acetic acid | 50 ml | 0.25 (7) | 100 | 86.7 | 76.5 | 6.39 |

(1) Conversion rate of hydroquinone
(2) Monochlorohydroquinone yield with respect to the hydroquinone converted
(3) Dichlorohydroquinone yield with respect to the hydroquinone converted.
(4) Isopropyl ether
(5) Butyl ether
(6) Ethyl ether
(7) 0.25 mole of hydroquinone had been added While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the essentially selective nascent chlorination of hydroquinone to monochlorohydroquinone, comprising reacting hydroquinone with an aqueous solution of hydrochloric acid and hydrogen peroxide, in the presence of an ether solvent for, and inert to, said hydroquinone.

2. The process as defined by claim 1, wherein said inert ether solvent is miscible with the aqueous hydrochloric acid solution.

3. The process as defined by claim 1, wherein said reaction is carried out in homogeneous liquid phase.

4. The process as defined by claim 1, said inert ether solvent comprising ethyl ether, n-propyl ether, isopropyl ether, n-butyl ether, dioxane, or diglyme.

5. The process as defined by claim 4, said inert ether solvent comprising isopropyl ether.

6. The process as defined by claim 1, wherein the concentration of said aqueous hydrochloric acid solution is at least 7 moles per liter.

7. The process as defined by claim 6, wherein the amount of hydrochloric acid is at least one mole thereof per mole of hydroquinone.

8. The process as defined by claim 7, wherein the amount of hydrogen peroxide ranges from 0.9 to 1.2 moles thereof per mole of hydroquinone.

9. The process as defined by claim 8, carried out at a temperature of from 0° to 150° C.

10. The process as defined by claim 1, comprising gradually adding on aqueous hydrogen peroxide solution to a homogeneous mixture of an aqueous hydrochloric acid solution and a solution of the hydroquinone in the inert ether solvent therefor.

11. The process as defined by claim 10, said gradual addition being under stirring.

* * * * *